United States Patent
Wang et al.

(10) Patent No.: US 7,173,701 B2
(45) Date of Patent: Feb. 6, 2007

(54) CCD-BASED BIOCHIP READER

(75) Inventors: Jiann-Hua Wang, Taipei (TW); Tsung-Kai Chuang, Tainan (TW); Tzu-Chiang Wu, Miaoli (TW); Chien-Ho Chuang, Kaohsiung (TW)

(73) Assignee: Kaiwood Technology Co., Ltd., Tainan County (TW)

( * ) Notice: Subject to any disclaimer, the term of this patent is extended or adjusted under 35 U.S.C. 154(b) by 365 days.

(21) Appl. No.: 10/777,651

(22) Filed: Feb. 13, 2004

(65) Prior Publication Data

US 2005/0179900 A1    Aug. 18, 2005

(51) Int. Cl.
G01J 21/64    (2006.01)

(52) U.S. Cl. .................................. 356/417; 250/458.1

(58) Field of Classification Search ............. 250/458.1, 250/459.1, 461.1; 356/417
See application file for complete search history.

(56) References Cited

U.S. PATENT DOCUMENTS 6,496,309 B1 * 12/2002 Bliton et al. ................ 359/618
6,542,241 B1 * 4/2003 Thorwirth et al. .......... 356/436
2002/0131618 A1 * 9/2002 Ahlers et al. ............... 382/101

FOREIGN PATENT DOCUMENTS

WO     WO 00/58715    * 10/2000

* cited by examiner

Primary Examiner—F. L. Evans
(74) Attorney, Agent, or Firm—Birch, Stewart, Kolasch & Birch, LLP

(57) ABSTRACT

A CCD-based biochip reader includes a light source for emitting light beams, a collimating lens for converting the light beams into wide parallel rays of light, passing said wide parallel rays of light through a biochip and exciting fluorescence from fluorescent targets on the biochip, a focusing lens for focusing the fluorescence, a filter for filtering out said parallel rays of light, and a charge-coupled device camera for generating images from said fluorescence. For recording intensity of the fluorescence from the fluorescent targets, images of the charge-coupled device camera is converted into digital data through an image converting device. Wide parallel laser beams are produced by the laser and through the collimating lens, and excite all samples on the biochip with high efficiency at the same time. In addition, time for analysis is saved when fluorescent images of a large area on biochips are collected and analyzed through the charge-coupled device camera.

5 Claims, 3 Drawing Sheets

CCD-BASED BIOCHIP READER

BACKGROUND OF THE INVENTION

1. Field of the Invention

The present invention relates to a CCD-based biochip reader, particularly to a biochip reader with a charge-coupled device (CCD) camera to collect and analyze images of fluorescence from biochips.

2. The Prior Arts

Tools and methods are designed to detect and analyze nucleic acids and proteins in the cellular and molecular biology field. However, it takes much time to complete analysis of a large number of samples. Moreover, errors arise since so many samples cannot be analyzed at the same time. For accelerating the progress of the related research, especially the genomic and proteomic research, high-throughput tools for efficient analysis are manufactured, of which an example is biochips. Biochips are applied to gene expression, drug selection and disease diagnosis in both basic research and clinical application fields.

There are three kinds of biochips that are currently known as DNA chip, lab-on-a-chip and protein chip. Since the protein chip and the lab-on-a-chip are difficult to operate, the DNA chip is in common use now. The detection of the DNA chip is shown in FIG. 1. First, known DNA fragments used as DNA probes (2) are immobilized onto the surface of a glass slide or a silicon chip and form a DNA chip (1). Generally, the DNA probes (2) arranged in array are called a DNA microarray. On the other hand, unknown DNA fragments (3), the target DNA, are labeled with fluorophores. The DNA chip (1) is hybridized with target DNA (3). After steps of washing, only DNA fragments hybridized with DNA probe are left on DNA chip (1). By scanning the DNA chip with a biochip reader, the fluorescence excited from the fluorophores is detected and the obtained hybridization result is analyzed.

Generally, a conventional biochip reader relies on laser excitation and a photomultiplier tube for detector (laser/PMT based systems) is employed to obtain representative images. FIG. 2 is a schematic view showing an example of the conventional biochip reader (4). Light beams emitted from a laser source (40) pass through a focusing lens (41), reflected by a beam splitter (42), and then passing through another focusing lens (43) to a surface of the biochip (44). The fluorescent dyes on the biochip (44) are excited by the light beams and in turn emit fluorescence (45). The fluorescence (45) passes through the focusing lens (43), the beam splitter (42), and the other focusing lens (46). The fluorescence (45) further passes through a filter (47), with which the light beams from the light source are filtered out. A detected photo signal is transmitted to a photomultiplier tube (PMT) (48), which converts the light pulse into an amplified electrical signal. Finally, the signal is fed to a computer (49) and processed to form image data. In the prior art biochip reader, to obtain the final result requires scanning all samples on the biochip, converting light pulses into electrical signals, and forming the electrical signal image data for analysis. The prior art biochip is disadvantageous for it takes a long time to scan all the samples and obtain the images.

The other kind of biochip reader uses white-light excitation with a high-pixel charge-coupled device (CCD) camera to collect images and analyze. Although it is not necessary to scan all the samples on the biochip in this kind of biochip reader, the white-light excitation is not efficient and the sensitivity is lower than the laser/PMT based systems. To enhance sensitivity, it takes a long time to obtain a more intensive fluorescent signal.

As mentioned above, the utility of the biochip analysis system will be increased if the results of the biochip reader are analyzed efficiently.

SUMMARY OF THE INVENTION

A primary object of the present invention is to provide a CCD-based biochip reader by which samples are excited with wide parallel laser beams and images are collected and analyzed through a large-area charge-coupled device camera. Therefore, detection is rapid and efficient.

In order to realize the foregoing objects, a CCD-based biochip reader of the present invention comprises: a light source for emitting light beams; a collimating lens for converting the light beams into wide parallel rays of light through a biochip and exciting fluorescence from fluorescent targets on the biochip (if the laser contains a collimator, it does not need to add this collimator); a focusing lens for focusing the fluorescence (if the CCD camera with a lens head, it does not need a focusing lens); a filter for filtering out said parallel rays of light; and a charge-coupled device camera for generating images from said fluorescence. For acquiring intensity of the fluorescence from the fluorescent targets, images of the charge-coupled device camera is converted into digital data through an image converting device.

Wide parallel laser beams are produced by the laser and through the collimating lens of the present invention, and excite all samples on the biochip with high efficiency at the same time. In addition, time for analysis is saved when fluorescent images of a large area on biochips are collected and analyzed through the charge-coupled device camera.

For more detailed information regarding advantages and features of the present invention, examples of preferred embodiments will be described below with reference to the annexed drawings. It is to be understood that both the foregoing general description and the following detailed description are exemplary and explanatory and are intended to provide further explanation of the invention as claimed.

BRIEF DESCRIPTION OF THE DRAWINGS

The related drawings in connection with the detailed description of the present invention to be made later are described briefly as follows, in which.

DETAILED DESCRIPTION OF THE PREFERRED EMBODIMENT

Figure 1:
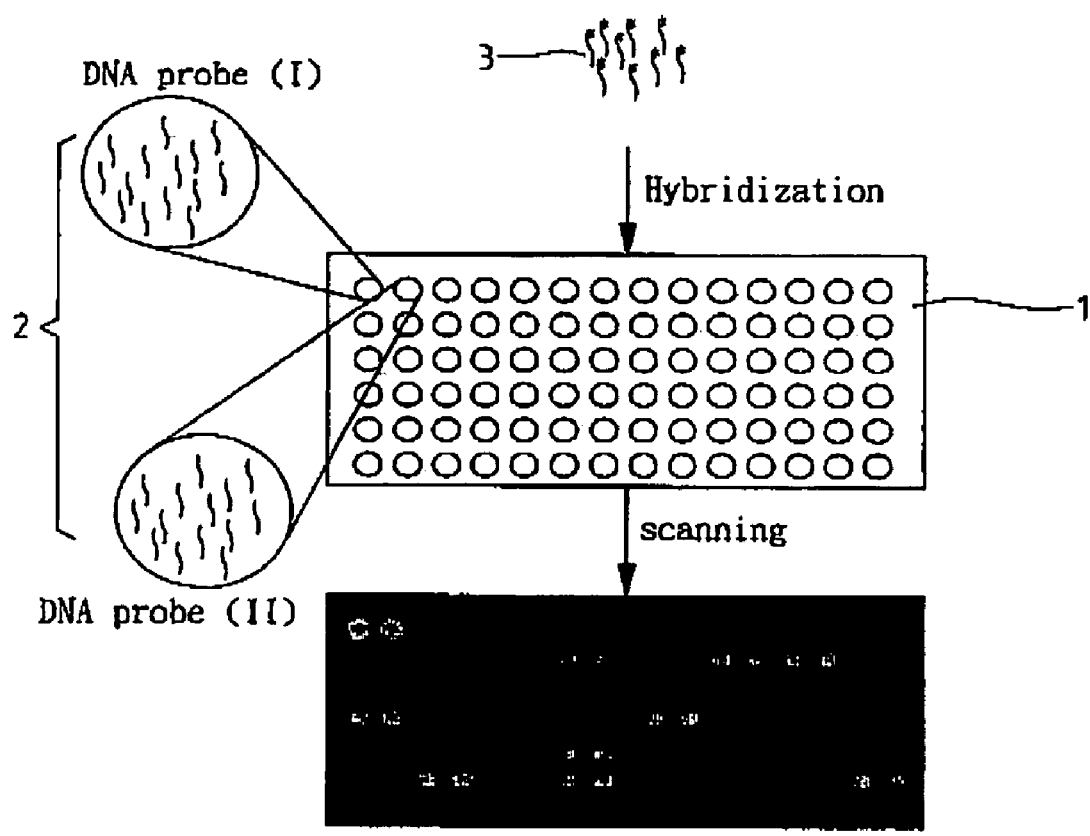
FIG. 1 illustrates a conventional DNA chip detection system.
Figure 2:
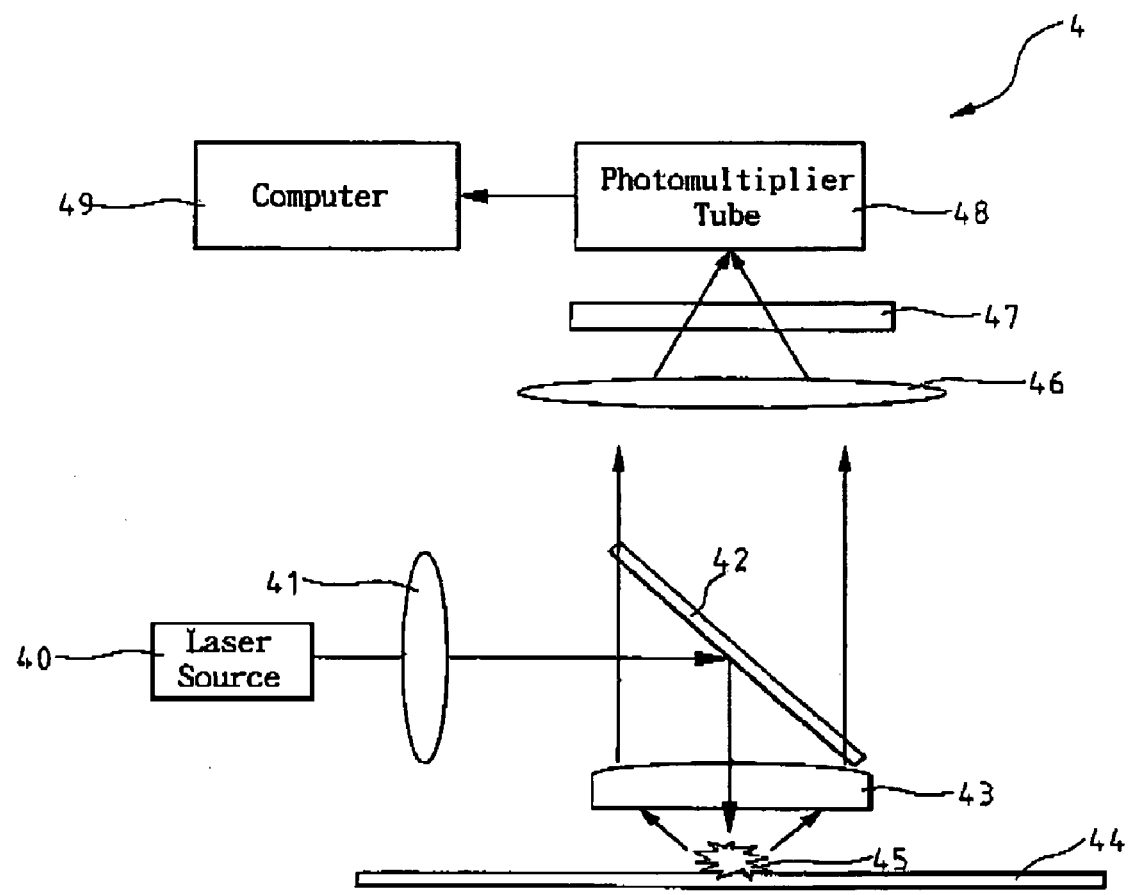
FIG. 2 is a schematic view showing an example of a conventional biochip reader.
Figure 3:
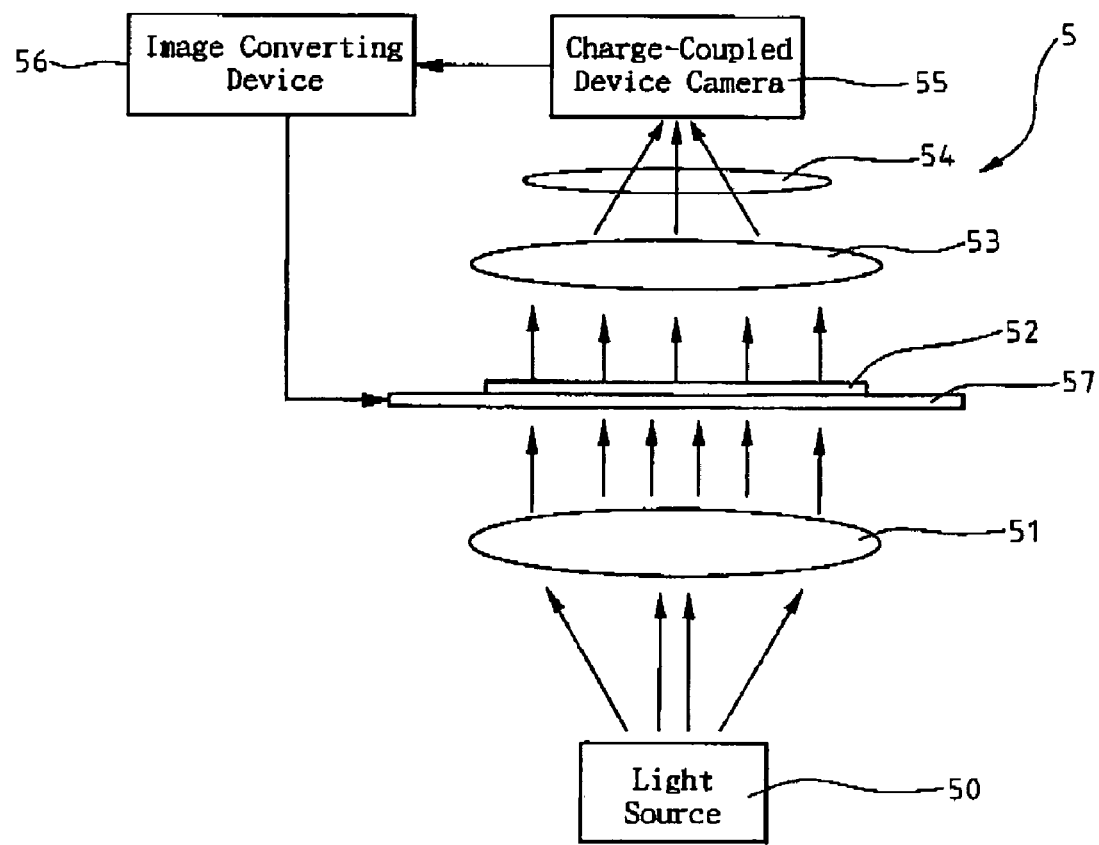
FIG. 3 is a schematic view showing an embodiment of the CCD-based biochip reader of the present invention.

Preferred embodiments of the present invention will now be described in detail below with reference to the accompanying drawings. FIG. 3 is a schematic view showing an embodiment of a CCD-based biochip reader (5) of the present invention. The CCD-based biochip reader (5) comprises a light source (50), such as a laser source, for emitting flat-top energy light beams, which means the energy distribution of the light beams is non-Gaussian (uniform) distribution in intensity; a collimating lens (51) for converting said light beams into wide parallel rays of light (if the laser contains a collimator, it does not need to add this collimator), passing said wide parallel flat-top energy rays of light through a biochip (52) and exciting fluorescence from fluorescent targets on the biochip (52); a focusing lens (53) for focusing the fluorescence (if the CCD camera with a lens head, it does not need a focusing lens); a filter (54) for filtering out said parallel rays of light; a large-area charge-coupled device camera (55) for collecting images from the fluorescence signal; a platform (57) for holding the biochip (52); and an image converting device (56) for converting the images into digital data. The digital data are used to record the intensity of the fluorescence.

Biochips are placed on the platform (57) first when analyzed by the CCD-based biochip reader of the present invention. When scanning, the flat-top energy light beams from the laser source (50) pass through the colliamting lens (51), and are transformed into wide parallel rays of light through a biochip (52) and excite fluorescence from fluorescent targets on the biochip (52). The fluorescence passes through a focusing lens (53) and a filter (54), by which the parallel rays of light are filtered out. Images are collected from a charge-coupled device camera (55). Finally, the resulted images are transferred to an image converting device (56) and converted into digital data. The digital data are used to record the intensity of the fluorescence. For the convenience of analysis, the image converting device (56) may be a computer, which comprises algorithm to control the platform (57) so that operation of the CCD-based biochip reader (5) is more easily.

As mentioned above, wide parallel flat-top energy laser beams are produced by the laser and through the collimating lens of the present invention, and excite all samples on the biochip with high efficiency at the same time. In addition, time for analysis is saving when fluorescent images of a large area on biochips are collected and analyzed through the charge-coupled device camera.

What is claimed is:

1. A CCD-bascd biochip reader comprising:
    a light source for emitting light beams, a collimating lens for converting said light beams into wide parallel rays of light, passing said wide parallel rays of light through a biochip and exciting fluorescence from fluorescent targets on said biochip;
    a focusing lens for focusing said fluorescence;
    a filter for filtering out said parallel rays of light; and
    a charge-coupled device camera for collecting images from said fluorescence,
    wherein said light beams comprise flat-top energy light beams whereby energy distribution of the light beams is a non-Gaussian distribution in intensity.

2. The CCD-based biochip reader according to claim 1, further comprising an image converting device for converting said images into digital data.

3. The CCD-based biochip reader according to claim 1, further comprising a platform for holding said biochip and selectively moving in one direction.

4. The COD-based biochip reader according to claim 3, further comprising a computer, wherein said computer comprises at least one set of parameters for controlling the directions of movement of said platform.

5. The CCD-based biochip reader according to claim 4, wherein said computer comprises at least one set of parameters for converting images of said charge-coupled device into digital data.

* * * * *